(12) United States Patent
Kim (10) Patent No.: US 9,744,198 B2
(45) Date of Patent: *Aug. 29, 2017

(54) **PHARMACEUTICAL COMPOSITION INCLUDING DEAD CELLS OF *LACTOBACILLUS ACIDOPHILUS* LB TO TREAT OR PREVENT ALLERGIC DISEASE**

(71) Applicant: Dae Hyun Kim, Seoul (KR)

(72) Inventor: Dae Hyun Kim, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 15/216,720

(22) Filed: Jul. 22, 2016

(65) Prior Publication Data

US 2016/0324906 A1 Nov. 10, 2016

Related U.S. Application Data

(63) Continuation of application No. 14/362,913, filed as application No. PCT/KR2012/007035 on Sep. 3, 2012, now Pat. No. 9,421,231.

(30) Foreign Application Priority Data

Dec. 19, 2011 (KR) .................. 10-2011-0137297

(51) Int. Cl.
  *A61K 35/74*  (2015.01)
  *A61K 35/747*  (2015.01)
  *A61K 9/00*  (2006.01)

(52) U.S. Cl.
  CPC .......... *A61K 35/747* (2013.01); *A61K 9/0053* (2013.01)

(58) Field of Classification Search
  None
  See application file for complete search history.

(56) References Cited

U.S. PATENT DOCUMENTS

| | | |
|---|---|---|
| 8,003,092 B2 | 8/2011 | Yamamoto et al. |
| 8,894,991 B2 | 11/2014 | Boileau et al. |
| 2002/0192202 A1 | 12/2002 | Naidu |
| 2007/0134220 A1 | 6/2007 | Servin et al. |
| 2008/0107699 A1 | 5/2008 | Spigelman et al. |
| 2008/0166331 A1 | 7/2008 | Su et al. |
| 2011/0027230 A1 | 2/2011 | Di Leo et al. |
| 2011/0106650 A1 | 5/2011 | Stone et al. |
| 2012/0039860 A1 | 2/2012 | Roughead et al. |

FOREIGN PATENT DOCUMENTS

| | | |
|---|---|---|
| EP | 1000625 A1 | 5/2000 |
| EP | 1941892 A2 | 7/2008 |
| KR | 10-2003-0021298 A | 3/2003 |
| KR | 10-2004-0068820 A | 8/2004 |
| KR | 10-2005-0001548 A | 1/2005 |
| KR | 10-2005-0014879 A | 2/2005 |
| KR | 10-2006-0096851 A | 9/2006 |
| KR | 10-2008-0018287 A | 2/2008 |
| WO | 2008/106373 A1 | 9/2008 |
| WO | 2010/077795 A2 | 7/2010 |

OTHER PUBLICATIONS

Jason, Y.S.K et al., Mental Health Initiatives in Singapore, Lacteol Fort Treatment Reduces Antibiotic Associated Diarrhea, Singapore Family Physician, Oct.-Dec. 2010, vol. 36(4), pp. 46-49.
Anuradha, S et al., JIACM, 2005, vol. 6(1), pp. 61-72, Probiotics in Health and Disease (Review Article).
Peng, G-C et al., Pediatric Allergy Immunology, 2005, vol. 16, pp. 433-438, The efficacy and safety of heat-killed Lactobacillus paracasei for treatment of perennial allergic rhinitis induced by house-dust mite.
Murch, SH. Toll of allergy reduced by probiotics, Lancet, vol. 357, pp. 1057-1059, 2001.
Abrahamsson, Thomas R et al., Probiotics in prevention of IgE associated eczema: A double blind, randomized placebocontrolled trial, Journal of Allergy Clinical Immunology, 2007, vol. 119, pp. 1174-1180.
National Medicines Comprehensive Database, Lactobacillus, pp. 1-14, updated Dec. 9, 2011.
Zuccotti, GV et al., Journal of International Medical Research, vol. 36, 2008, pp. 1-54, Probiotics in Clinical Practice: An Overview.
Sullivan, Asa et al., Nutritional Journal, pp. 1-6, Jan. 26, 2009, vol. 8(4), Effect of supplement with lactic-acid producing bacteria on fatigue and physical activity in patients with chronic fatigue syndrome.
Alfonso et al., "Preliminary evidence of the efficacy of probiotic eye-drop treatment in patients with vernal . . . ", Graefes Arch Clin Exp Ophthalmol (2008) 246:435-441.
Rasche et al., "Oifferential immunomodulating effects of inactivated probiotic bacteria on the allergic immune response.", Acta Denn Venereol 2007; 87: 305-311.
The extended European search report for EP application No. 12859838 dated Jun. 1, 2015 from European Patent Office.
Coconnier, M et al., Antimicrobial Agents and Chemotherapy, May 1997, pp. 1046-1052, vol. 41 (5), Antibacterial Effect of the adhering human *Lactobacillus acidophilus* Strain LB.
Chauviere, Gilles et al., Journal of General Microbiology, 1992, vol. 138, pp. 1689-1696, Adhesion of human *Lactobacillus acidophilus* strain LB to human enterocyte-likeCaco-2 cells.
Mastrandrea, Fet al., Probiotics reduce the CD34+ hemopoietic precursor cell increased traffic in allergic subjects, vol. 36(4), 2004, pp. 118-122.
Ishida, Y et al., J. Dairy Science, vol. 88, pp. 527-533, Clinical Effects of *Lactobacillus acidophilus* Strain L-92 on Perennial Allergic Rhinitis: A Double Blind, Placebo-Controlled Study.
Ouwehand, AC et al., World Journal of Gastroenterology, Jul. 14, 2009, vol. 15(26), pp. 3261-3268. Specific probiotics alleviate allergic rhinitis during the birch pollen season.

(Continued)

*Primary Examiner* — Jennifer Graser
(74) *Attorney, Agent, or Firm* — Revolution IP, PLLC (57) ABSTRACT

Disclosed is a pharmaceutical composition including dead cells of *Lactobacillus acidophilus* LB strain as an active ingredient for treating or preventing an allergic disease, and may be used to treat and prevent IgE-mediated allergic diseases and non-IgE-mediated allergic diseases such as atopic dermatitis, allergic rhinitis, allergic conjunctivitis, urticaria, and pollinosis by reducing the total content of IgE in the blood.

6 Claims, 4 Drawing Sheets

(56) References Cited

OTHER PUBLICATIONS

Charng, Y et al., VAccine, vol. 24, 2006, pp. 5931-5936.
Roessler, A et al., Clinical and Experimental Allergy, vol. 38, pp. 93-102, 2007.
Repa, A et al., VAccine, vol. 22, pp. 87-95, 2003.
Taylor, AL et al., Clinical and Experimenal Allergy, vol. 36, pp. 1227-1235, 2006.
Kim, JY et al., Pediatric Allergy and Immunology, vol. 21, pp. 3386-3393, Mar. 2010.
Jason, YSK et al., Mental Health Initiatieves in Singapore, 2010, vol. 36(4) pp. 46-49.
Rasche, C et al., ACTA Derm. Venereol. 2007, vol. 87, pp. 305-311.
Simakachom, N. et al., Journalf of Pediatric Gastroenterology and Nutrition, Jan. 2000, vol. 30, pp. 68-72.
Taylor, A.L. et al., Journal of Allergy and Clinical Immunology, 2007, vol. 119, pp. 184-191.

PHARMACEUTICAL COMPOSITION INCLUDING DEAD CELLS OF *LACTOBACILLUS ACIDOPHILUS* LB TO TREAT OR PREVENT ALLERGIC DISEASE

CROSS REFERENCE TO PRIOR APPLICATIONS

This application is a Continuation of U.S. patent application Ser. No. 14/362,913 filed Jun. 4, 2014, which is a National Stage Application of PCT International Patent Application No. PCT/KR2012/007035 filed Sep. 3, 2012, under 35 U.S.C. §371, which claims priority to Korean Patent Application No. 10-2011-0137297 filed Dec. 19, 2011, which are all hereby incorporated by reference in their entirety.

BACKGROUND

The present invention relates to a pharmaceutical composition for treating or preventing an allergic disease, and particularly, a pharmaceutical composition for treating or preventing an allergic disease, which includes dead cells of *Lactobacillus acidophilus* LB as an active ingredient.

It is known that allergic diseases are largely divided into immunoglobulin (IgE)-mediated diseases and non-IgE-mediated diseases. It is known that when allergens triggering an allergic disease are penetrated into a body, the allergic disease is triggered and worsened by imbalance of Th(helper)1/Th(helper)2 lymphocytes.

In addition, it is known that abnormal differentiation of Th2-cells is induced by action of a cytokine including IL-4 (according to the recent study, when production of IL-4 and IL-5 are reduced, an allergic disease is not improved, and thus IL-4 and IL-5 are also known as unimportant factors in triggering of the allergic disease), cytokines including IL-9, IL-33, and thymic stromal lymphopoietin (TSLP), regulatory T-cell (Treg) families (nTreg, Th3, and iTreg), and newly known effecter cells such as nuocytes, Th9, and Th22, which induce Th2 differentiation.

When microorganisms or chemicals and allergens are penetrated, rather than that TSLP, as a primary inducer of Th2 immune deviation, is produced by epitheliums in the skin, intestines, and lung to stimulate dendritic cells, thereby stimulating production of Th-2 cytokine and directly producing cytokines, a TSLP-primed dendritic cells (DCs) serve to up-regulate costimulatory molecules (molecules of antigen presenting cells) and increase production of Th2-attracting chemokines including thymus and activation-regulated chemokine (CCL17), macrophage-derived chemokine (CCL22), IL-15, and IL-18. Similarly, in the skin, TSLP expression provokes atopic dermatitis.

Meanwhile, large amounts of keratinocytes are expressed in atopic dermatitis patients. That is, an allergen induces amplification of TSLP-mediated Th2 response. When production of IL-25 is increased by an allergen, production of CCL5 (RANTES) and CCL11 (eotaxin-1) is increased, and thus eosinophils remain at a part in which inflammation occurs. In addition, interleukin-33 (IL-33) secreted from necrotized cells generated by reaction to infection and inflammation is expressed in bronchial epithelium, fibroblast, keratinocytes, smooth muscle cells, dendritic cells, mast cells, and macrophages, and serves as a chemoattractant to Th2 cells, in addition to Th2 immune deviation. When IL-33 is administered, Th2 immune deviation, cytokine production, elevated IgE, and mucosal eosinophilic inflammation are induced to cause DC differentiation, thereby inducing expression of major histocompatibility complex class 2, CD86, and IL-6. The activated DC as described above stimulates differentiation of naive CD4+T cells to increase production of IL-5 and IL-13, and IL-33 helps in maturation of a CD34+ mast cell precursor and homing to a tissue. As a result, activation of IL-25, IL-33, and TSLP that are imbalanced in inducing and worsening an allergic disease results in allergic diseases through a pathological and inflammatory process of allergic diseases due to activation of cells inducing and worsening the allergic diseases such as Th cells, mast cells, DCs, eosinophils, and basophils.

As the allergic diseases, atopic dermatitis, allergic rhinitis, allergic conjunctivitis, rash, pollinosis, or asthma is known.

It is reported that atopic dermatitis is expressed 50% at the age of 1, and 80% at the age of 5, and usually is shown as a chronic, relapsing skin disease, for example, eczema on the folds of a body such as antecubital fossa or popliteal fossa. Usually, IgE is increased in a serum, and allergic rhinitis and asthma are accompanied as a person grows. Prevalence in the developed countries varies depending on a reporter in a range from 20 to 30%, and it is reported that in Korea, prevalence is 10% at the age of 6 or less, 6% at the age of 6 to 12, and generally 2% at the age of 20 or more. The atopic dermatitis is classified into an intrinsic type or an extrinsic type according to a clinical phenotype, and depending on a reporter, the prevalence of the intrinsic dermatitis varies in the range of 10 to 30.4%, and clinical characteristics of the intrinsic dermatitis determined by a skin prick test are normal in total IgE level in serum, negative in allergy-inducing food, and negative in allergen-specific serum IgE with respect to general aeroallergens and food allergens. The extrinsic atopic dermatitis has the highest frequency at the age of 18 or more, averagely 31.6, and the intrinsic atopic dermatitis has the highest frequency at the average age of 27.1. The average age of total patients with intrinsic dermatitis is 30.4, and it is reported that the frequency is considerably reduced according to time, and the intrinsic dermatitis barely occurs over 57 or more years old. In addition, it was reported that 57.8% of patients with atopic dermatitis was accompanied with allergic conjunctivitis or asthma, 61.7% of the patients were increased in total IgE, 26.5% of the patients had a total IgE of 300 IU/ml or more, and 36.7% of the patients had $1^{st}$-degree relatives.

In addition, allergic rhinitis is a symptomatic disorder of the nose inducing an IgE-mediated inflammation after allergen exposure, and causing symptoms in a nose, eyes, ears, and fauces. Previously, it was classified into seasonal or perennial allergic rhinitis, but presently is divided into intermittent allergic rhinitis or persistent allergic rhinitis, and subdivided into mild, moderate, or severe allergic rhinitis based on duration of symptoms by "the Allergic Rhinitis and Its Impact on Asthma Working Group." The prevalence is 10 to 30% in adults, and approximately 40% in children, which are a bit different according to a reporter in each country. Allergic rhinitis risk factors are indoor and outdoor allergens and when serum IgE is 100 IU/ml or more before the age of 6. Allergic rhinitis develops complications such as sinusitis, otitis media, conjunctivitis, and sleep disturbance, an attention problem, and maladjustment of a social life due to exacerbation of asthma and sinusitis when not treated and thus becoming worse.

In addition, urticaria is a disease temporarily expressing well-circumscribed wheals in red or white on a superficial portion of dermis and mucosa. When the symptoms do not persist 6 weeks, it is defined as acute urticaria, and when persisting over 6 weeks, it is defined as chronic urticaria. The urticaria is caused by internal and external factors, and mostly foods, drugs, food additives, and infectious and physical stimuli (cold, heat, exercise, solar rays, and mechanical irritation) are estimated as main causes. Inhalants such as pollen, animal dander or fur, spores of fungi, house dust mites, air sprays, etc. are inhaled through respiration to cause urticaria, and foods are generally causes of acute urticaria, but barely induce chronic urticaria. As foods that frequently cause urticaria, chocolates, clams (particularly, Meretrix lusoria), peanuts, peas, chestnuts, tomatoes, kiwis, egg whites, cheeses, garlic, onions, and food additives [yeast, salicylic acid, citric acid, azo dyes, or benzoic acid derivatives] are used, and as drugs, various drugs such as aspirin, sulfone amide, narcotic, NSAID, vitamin, estrogen, insulin, quinine, salicylate, etc. are used. The urticaria is easily diagnosed only by clinical symptoms, and if it is difficult to find a cause, various examinations may be helpful to find the cause. For treatment, avoidance after finding a cause is ideal, but since it is difficult to find a cause, various public remedies are performed.

To treat such an allergic disease, various therapies are being studied, and anti-allergic agents, histamine receptor antagonists (antihistamines), steroids, etc. are used. However, any one of an antihistamine inhibiting signal transduction from peripheral nerves by being linked with a histamine receptor antagonistically to histamine, an anti-allergic agent reducing an activity of chemical mediator-producing cells to attempt alleviation of symptoms, and a steroid reducing immune responses to alleviate inflammation has side effects, but there is no dramatic effect.

Meanwhile, lactobacilli is a product first found by Metchnikoff and obtained from attempts to obtain a therapeutic effect by acidifying intestinal contents to prevent growth of putrefactive organisms, and 165 species of *Lactobacillus* genera considered as representative lactobacilli are found. Particularly, as a probiotic *lactobacillus* which has been used in treatment of an allergic disease, it has been reported that *Lactobacillus acidophilus* L-92 has effects on some of allergic rhinitis symptoms triggered by Himalayan cedar pollens in Japan, and use of *Lactobacillus rhamnosus* GG, *Lactobacillus acidophilus* species, *Lactobacillus reuteri* species, *Lactobacillus fermentum* species, *Bifidobacterium breve* species, or *Bifidobacterium lactis* species has been attempted to treat atopic dermatitis.

As *Lactobacillus acidophilus* species strains separated from a human intestine among the strains of the *Lactobacillus* genera, strains clinically used for treatment such as *Lactobacillus acidophilus* LB strain, *Lactobacillus acidophilus* 145 strain, *Lactobacillus acidophilus* DDS-I strain, *Lactobacillus acidophilus* L-92 strain, *Lactobacillus acidophilus* NCFM strain, *Lactobacillus acidophilus* LA O2 strain, *Lactobacillus acidophilus* L-55 strain, *Lactobacillus acidophilus* NCK56 strain, *Lactobacillus acidophilus* CH5 strain, *Lactobacillus acidophilus* LAFTIL-10 strain, *Lactobacillus acidophilus* OLL2769 strain, and *Lactobacillus acidophilus* 27L strain were used. Among these, only two kinds of the strains such as *Lactobacillus acidophilus* DDS-1 strain and *Lactobacillus acidophilus* NCFM strain were used in treatment of an allergic disease, but an effect on treating or improving an allergic disease was not proved.

Meanwhile, Lacteol is a product name of a freeze-dried product of a culture solution containing tyndallized dead cells of *Lactobacillus acidophilus* LB strain found by the French doctor, Pierre BOUCARD, in 1907, and a dead cell drug conserving a metabolite produced by *Lactobacillus acidophilus* LB strain, which is known as a safe drug having no fatal side effects since it was produced in 1979 and no fatal reports with long-term use, is known to be effective in acute diarrhea and diarrhea caused by colitis and functional colonic diseases, but it was never used in treatment of an allergic disease.

The inventor found that Lacteol containing dead cells of *Lactobacillus acidophilus* LB strain had excellent therapeutic effects and improvements in symptom, compared to the primary therapeutic agents of atopic dermatitis, calcineurin inhibitors, a therapeutic agent to allergic rhinitis, antihistamines, and intranasal inhalants, and therefore the present invention was completed.

SUMMARY

The present invention is directed to providing a pharmaceutical composition for treating or preventing an allergic disease without a side effect.

One aspect of the present invention provides a pharmaceutical composition for treating or preventing an allergic disease, which includes dead cells of *Lactobacillus acidophilus* LB strain as an active ingredient.

In the pharmaceutical composition for treating or preventing an allergic disease of the present invention, the dead cells are provided in the form of a culture solution containing tyndallized dead cells of the *Lactobacillus acidophilus* LB strain.

In the pharmaceutical composition for treating or preventing an allergic disease of the present invention, the dead cells are provided in the form of a freeze-dried product of the culture solution containing tyndallized dead cells of the *Lactobacillus acidophilus* LB strain.

In the pharmaceutical composition for treating or preventing an allergic disease of the present invention, the pharmaceutical composition is orally administered.

In the pharmaceutical composition for treating or preventing an allergic disease of the present invention, the pharmaceutical composition is a dead cell, 1 to 10 billion of which are orally administered a day.

In the pharmaceutical composition for treating or preventing an allergic disease of the present invention, the pharmaceutical composition reduces a total IgE content in the blood through oral administration.

In the pharmaceutical composition for treating or preventing an allergic disease of the present invention, the allergic disease is atopic dermatitis, allergic rhinitis, allergic conjunctivitis, urticaria, pollinosis, or asthma.

In the pharmaceutical composition for treating or preventing an allergic disease of the present invention, the pharmaceutical composition is prepared in a tablet, a capsule, a granule, a powder, or a liquid.

A pharmaceutical composition of the present invention includes dead cells of *Lactobacillus acidophilus* LB strain as an active ingredient to reduce a total IgE content in the blood without a side effect, and can be used to treat and prevent IgE-mediated allergic diseases and non-IgE-mediated allergic diseases, for example, atopic dermatitis, allergic rhinitis, allergic conjunctivitis, urticaria, and pollinosis.

DETAILED DESCRIPTION

The present invention provides a pharmaceutical composition for treating or preventing an allergic disease containing dead cells of *Lactobacillus acidophilus* LB strain as an active ingredient.

The *Lactobacillus acidophilus* LB strain of the present invention is isolated from human feces, and registered under MA65/4E to French National Collection of the Pasteur Institute (CNCM).

The dead cells of the *Lactobacillus acidophilus* LB strain of the present invention are cells killed by thermal treatment, and normally prepared by heating live cells at 70 to 90° C. higher than a dry temperature. Preferably, the dead cells of the present invention are a culture solution containing dead cells obtained by repeatedly heating cells by intermittent thermal treatment called tyndallization. For example, the dead cells may be prepared by freeze-drying a culture solution containing dead cells prepared by inoculating and culturing LB strains in whey broth at 37° C. for 3 days and heating the broth at 75° C. for 15 minutes a day, thereby killing spores.

The term "contained as an active ingredient" used herein means that dead cells of the *Lactobacillus acidophilus* LB strain are contained in a sufficient amount to achieve a treating or preventing effect on an allergic disease. In one exemplary embodiment of the present invention, a content of dead cells of the *Lactobacillus acidophilus* LB strain is 100 million or more cells/g, preferably 1 to 10 billion cells/g in the pharmaceutical composition of the present invention. The dead cells of the *Lactobacillus acidophilus* LB strain of the present invention has no specific side effect on a human, except loose feces, and thus a quantitative upper limit of the dead cells of the *Lactobacillus acidophilus* LB strain included in the pharmaceutical composition of the present invention may be selected within a suitable range by one of ordinary skill in the art.

The pharmaceutical composition of the present invention may be orally administered, and a suitable dosage of the pharmaceutical composition of the present invention varies according to factors such as a formulation method, an administration method, age, body weight, sex, a diseased condition of a patient, food, administration time, an administration route, an excretion speed, and reaction sensitivity, and ordinarily trained doctors can easily determine and prescribe a dosage effective in desired treatment or prevention. According to an exemplary embodiment of the present invention, a daily dosage of the pharmaceutical composition of the present invention is 1 to 10 billion, preferably, 5 to 8 billion dead cells based on an adult for oral administration. In infants or younger children, based on a body weight ranging from 20 to 40 kg, approximately ½ of the adult dosage may be administered, and based on a body weight of less than 20 kg, approximately ¼ of the adult dosage may be administered. The pharmaceutical composition of the present invention may be administered at the daily dosage once to twice a day.

The pharmaceutical composition of the present invention may be formulated using a pharmaceutically available carrier and/or excipient, and prepared in a unit capacity or contained in a high-dosage container according to a method that can be easily executed by one of ordinary skill in the art. Here, a dosage form may be a tablet, a capsule, a granule, powder, or liquids such as an aqueous medium-containing solution, a suspension, or an emulsion.

For example, to formulate the pharmaceutical composition in the form of a tablet or capsule, the active ingredient may bind to an oral, non-toxic pharmaceutically available inactive carrier such as ethanol, glycerol, water, etc. In addition, when desired or needed, a suitable binding agent, lubricant, disintegrating agent, coloring agent, or a mixture thereof may be included. The suitable binding agent may be, but is not limited to, natural sugar such as starch, gelatin, glucose, or beta-lactose, a natural or synthetic gum such as corn sweetener, acacia, Tragacanth, or sodium oleate, sodium stearate, magnesium stearate, sodium benzoate, sodium acetate, or sodium chloride. The disintegrating agent includes, but is not limited to, starch, methyl cellulose, agar, bentonite, or xanthan gum.

As pharmaceutically available carriers for the composition prepared in a liquid, those suitable for sterilization and a living body, a saline, sterilized water, a Ringer's solution, a buffered saline, an albumin injection, a dextrose solution, a maltodextrin solution, a glycerol, ethanol, or a mixture of at least one thereof may be used, and conventional additives such as antioxidants, buffers, bacteriostats, etc. may be added when needed.

Furthermore, as a suitable method used in a corresponding art, using a method disclosed in Remington's Pharmaceutical Science, Mack Publishing Company, Easton Pa., the pharmaceutical composition is preferably formulated according to a disease or component.

The pharmaceutical composition of the present invention reduces a total IgE content in the blood by oral administration. Accordingly, the pharmaceutical composition of the present invention may be used in treatment and prevention of an IgE-mediated allergic disease and a non-IgE-mediated allergic disease, for example, atopic dermatitis, allergic rhinitis, allergic conjunctivitis, urticaria, and pollinosis.

The present invention is not limited to cases that will be described below, but will be realized in various different types. The cases are merely provided to completely describe the scope of the present invention to those of ordinary skill in the art, and the present invention is only defined by the scope of the claim.

In a clinical trial of the present invention, as a culture solution containing tyndallized dead cells of *Lactobacillus acidophilus* LB strain, Lacteol (tablet) produced by Lacteol in France, and purchased from Dongwha Pharm. Co. Ltd was used. One tablet of Lacteol (1 tablet/g) includes 2.5 billion tyndallized dead cells of *Lactobacillus acidophilus* and has an apparent effect in diarrhea, and thus 4 to 8 tablets are recommended daily to an adult with acute diarrhea or irritable bowel syndrome having a primary symptom of diarrhea.

However, the fact that Lacteol affects an allergic disease, and a dosage of Lacteol have not been known. The inventor confirmed whether Lacteol had therapeutic effects on an allergic disease when at a low dosage of approximately ½ to ¼ the dosage for acute diarrhea: 2 tablets daily in adults, 1 tablet daily in older children having a body weight of 20 to 40 kg, and a ¼ tablet daily in younger children or infants having a body weight of less than 20 kg.

Clinical trials were carried out in a total of 34 patients with allergic diseases at the age ranging from 3 to 70, and a follow-up was performed for averagely 1 to 2 months since Lacteol had been administered.

Many scales to assess a clinical progress and therapeutic effects for atopic dermatitis are reported. Representatively, there are Eczema Area and Severity Index (EAST), SCORing Atopic Dermatitis (SCORAD), Patient Oriented Eczema Measure (POEM), and Three Item Severity (TIS). In the clinical trial, the TIS scale widely known as a prescreening system or quick system was used. The TIS scale consists of three items: erythema (redness), edema, and excoriation (scratches), and each item is graded on a scale 0 to 3 points: 0 point represents no change, 1 point represents mild, 2 points represent medium, and 3 points represent severe intensity, and the maximum point is 9. Severity of atopic dermatitis scored by the TIS scale is classified into a mild form (0 to 2 points), a moderate form (3 to 5 points), or a severe form (6 to 9 points) [Practical issues on interpretation of scoring atopic dermatitis: the SCORAD index, objective SCORAD, and the three-item severity score—review article].

In addition, allergic rhinitis is an indicator for a clinical process and a therapeutic effect, and various scales are known, and in clinical cases provided herein, a symptom scale (SS) was used among various scales applied to "Using the Congestion Quantifier Seven-Item Test to Assess Change in Patient Symptoms and Their Impact" disclosed in Allergy Asthma Proc 29:295-303, 2008. The SS consists of nine items, including four primary symptoms of allergic rhinitis and five symptoms accompanied with allergic rhinitis. For example, rhinitis symptoms consisting of nasal discharge, nasal congestion/stuffiness, nasal itching, and sneezing; and non-rhinitis symptoms consisting of itching/burning eyes, tearing/watering eyes, redness of eyes, itching of ears or palate and cough, and severity is rated on a 4-point scale: 0=none; 1=mild; 2=moderate; and 3=severe. Total SS is given by summarizing scores of the nine items.

Other than the above-described nine items, urticaria and acne, skin whitening and improvement were determined by photographs and with the naked eye.

Hereinafter, 34 cases will be described in detail, real names of patients except their last names were removed, males were described as M and females were described as F, and the age was shown behind the sex.

Total IgE was carried out in adult patients consenting to blood-gathering among patients with severe atopic dermatitis or allergic rhinitis, and lesions before and after treatment in all of the 34 patients were photographed to compare and stored as supporting evidences. Among the photographs, by comparing only the photographs of the patients in the cases 1, 9, 18 and 25 before and after treatment, a degree of improvement was easily identified, and then the photographs were attached to the specification as drawings.

Case 1) Jung 00 (f/26)

Over 20 years, the patient had been suffering from severe atopic dermatitis, and visited the hospital on Sep. 6, 2011. At the visit, severe edema, erythema, and excoriation were shown on the neck, antecubital fossa, popliteal fossa, etc., the TIS score of atopic dermatitis was 9, and total IgE was checked at 5326 IU/ml, which seemed very high.

Figure 1:
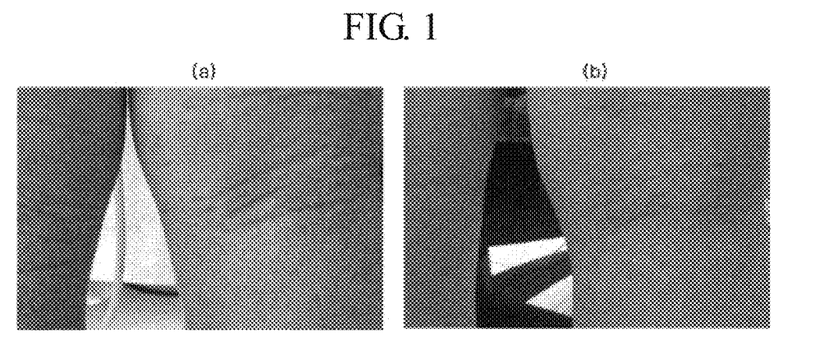
FIG. 1 shows images of popliteal fossa of a patient with atopic dermatitis in Case 1 before treatment (a) and after treatment (b)
Figure 2:
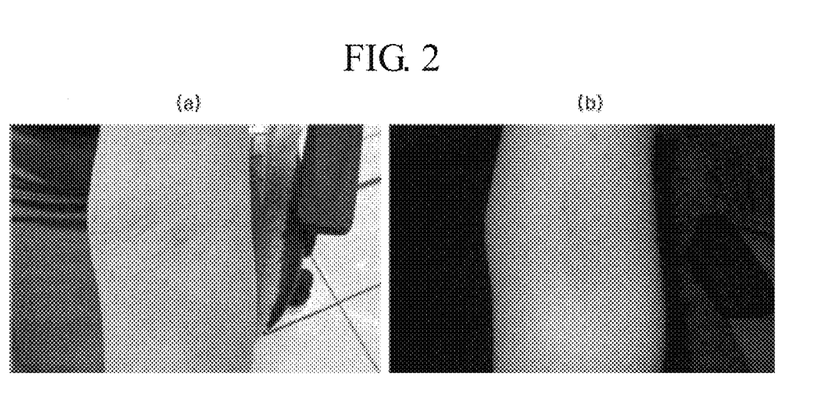
FIG. 2 shows images of antecubital fossa of a patient with atopic dermatitis in Case 1 before treatment (a) and after treatment (b)

Two tablets of Lacteol daily were administered, the total IgE measured at the second visit on October 5 was greatly reduced to 3906.7 IU/ml, and atopic lesions were graded as erythema (1 to 2 points), edema (1 to 2 points), and excoriation (1 to 2 points) by TIS as confirmed in photographs of legs before and after treatment in FIG. 1 and photographs of arms before and after treatment in FIG. 2, which indicated that atopic lesions had a mean TIS score of approximately 4 to 5 points, and were considerably improved to moderate lesions within one month of treatment.

At the third visit on November 10, a little erythema remained on the popliteal fossa and the frontal neck, and total TIS of all of the lesions were further improved to milder lesions having a score of approximately 1 to 2 points. At the third visit, the lesions became more apparently improved, and there was no side effect during the administration of Lacteol.

Case 2) Kim 00 (m/49)

The patient visited the hospital on Aug. 23, 2011 for weight loss and thirst, while suffering from severe pruritus caused by atopic dermatitis for 10 or more years, particularly, severe erythema, scratching, and severe itching on both shins, and nasal stuffiness (3 points), sneezing (2 points), and nasal discharge (2 points) caused by allergic rhinitis. At the visit, total IgE carried out under the doubt of diabetes (HbA1C-13.6) and atopy was measured at 544.6 IU/ml, atopic dermatitis on the both shins was graded as erythema (3 points), edema (1 point) and excoriation (2 to 3 points) by TIS, and atopic dermatitis on the right side of the face were graded as erythema (2 to 3 points) and edema (1 to 2 points) by TIS.

Combining with diabetes treatment, two tablets of Lacteol were administered daily, total IgE carried out at the second visit on September 26 was reduced to 300.6 IU/ml, atopic dermatitis triggered mild erythema, edema, and scratching on both shins, graded as 0 to 1 point by TIS, and erythema and edema on the face area were greatly decreased and became brighter. Pruritus all over the body was so improved that it was barely noticed, and during the administration of Lacteol, there was no specific side effect.

Case 3) Song 00 (m/52)

The patient visited the hospital on August 8 for cough. Total IgE carried out under the doubt of asthma and allergic rhinitis was checked at 957.1 IU/ml, and the patient had severe pruritus, and allergic rhinitis accompanied with symptoms including nasal stuffiness (3 points), nasal discharge (2 points), sneezing (2 points), and nasal itching (3 points) for 3 to 4 years. In addition, the rhinitis symptoms had total SS of 10 points, which were severe.

Two tablets of Lacteol were prescribed daily, and total IgE carried out at the second visit on September 30 was reduced to 593.6 IU/ml, the allergic rhinitis symptoms including nasal stuffiness (1 point), nasal discharge (1 point), sneezing (1 point), and nasal itching (1 point) were reduced, resulting in showing mild severity. The whole body pruritus was highly improved and thus barely noticed, and there was no discomfort caused by the Lacteol administration until the time of the visit.

Case 4) Gu 00 (m/36)

The patient visited the hospital on Oct. 13, 2011 for urticaria distributed on the entire body whenever he sweated for approximately 3 years. Total IgE carried out at the visit was a bit increased to 91.6, and overall, 2 to 3 mm small wheals were distributed on large erythematous redness.

Two tablets of Lacteol were prescribed daily, and since total IgE was low at the first visit, it was not measured at the second visit on November 9, and as therapeutic effects on cholinergic urticarial lesions, erythematous redness and small wheals were notably decreased on his back, left side of the face, and left antecubital fossa. In addition, pruritus became also alleviated, and there was no side effect at the visit.

Case 5) Yu 00 (f/50)

The patient visited the hospital on Sep. 19, 2011, while treated and taking a drug in an ophthalmology clinic for allergic conjunctivitis 1 week ago because of uncured allergic rhinitis and conjunctivitis suffering for approximately 12 years. At the visit, according to SS, allergic rhinitis was graded as nasal stuffiness (3 points), nasal discharge (2 points), nasal itching (3 points), eye redness (2 to 3 points), eye itching (3 points), and eye tearing (2 points). Since she took an antihistamine before coming to the hospital, total IgE was 409.2 IU/ml, which was otherwise considered higher.

Two tablets of Lacteol were administered daily, and at the second visit on November 8, total IgE was reduced to 313.2 IU/ml, and according to SS, allergic rhinitis were considerably improved to be mild severity and graded as nasal stuffiness (1 point), nasal discharge (1 point), nasal itching (1 point), eye redness (0 point), eye itching (0 to 1 point), and eye tearing (1 point), and eye redness and whitish scaly erythematous redness on the left neck and the frontal area were likely to be highly improved, and there were no specific side effects during treatment.

Case 6) Jung 00 (m/10)

The patient was a son of Yu 00 (F/50) of Case 5) and visited the hospital on September 28. While he had been treated in a dermatology clinic, at the visit, he had lesions on the left popliteal fossa, graded as erythema (2 points), edema (2 points), and excoriation (1 to 2 points) by TIS.

Since his body weight was less than 40 kg, one tablet of Lacteol daily was prescribed. The lesions seemed to be considerably improved and graded as erythema (0 to 1 point), edema (0 point), and excoriation (1 point) by TIS carried out at the second visit on November 9, and there was no side effect.

Case 7) Oh 00 (m/53)

The patient visited the hospital on Sep. 16, 2011 while treated in a dermatology clinic for atopic dermatitis and pruritus. At the visit, total IgE was 471.9 IU/ml, and lesions were on the back of the right and left ears, and around the chins, and graded as erythema (1 to 2 points), edema (1 to 2 points), and excoriation (1 point) by TIS.

Two tablets of Lacteol daily were prescribed, and total IgE carried out at the second visit on November 4 was a little reduced to 450.6 IU/ml. It was determined that the fact that the total IgE was relatively lower than those of other patients was because the total IgE was already decreased at the first visit due to administration of a drug prescribed in the dermatology clinic. At the second visit, the lesions were considerably improved and graded as erythema (0 to 1 point), edema (0 point), and excoriation (0 point) by TIS, and there was no specific side effect.

Case 8) Kim 00 (f/50)

The patient visited the hospital on Aug. 27, 2011 for atopic dermatitis over 10 years. Total IgE carried out at the visit was 14.4 IU/ml, which was in the normal range. Since she continuously administered antihistamine prescribed in a dermatology clinic, it was not known whether the atopic dermatitis was or was not intrinsic atopic dermatitis, and lesions on elbows and right antecubital fossa, etc. were graded as erythema (2 to 3 points), edema (2 to 3 points), and excoriation (2 to 3 point) by TIS.

Two tablets of Lacteol were administered daily, and at the second visit on November 5, almost all of the lesions disappeared, and there was no side effect.

Case 9) Cho 0 (m/28)

Figure 3:
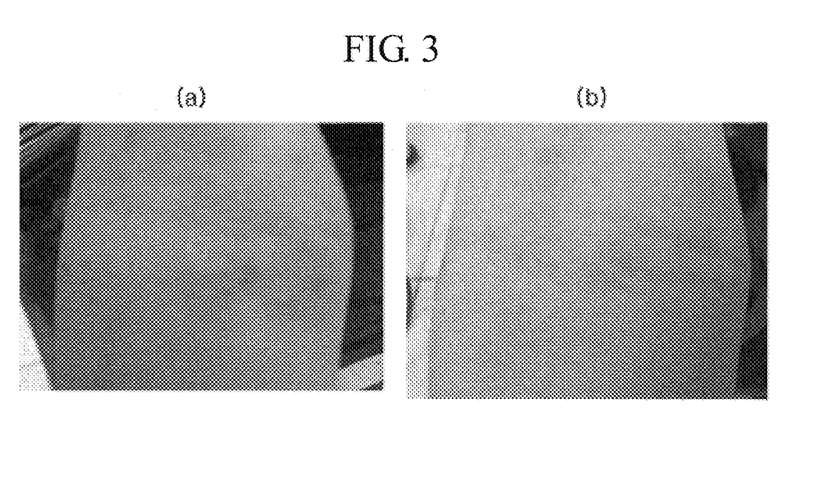
FIG. 3 shows images of the back area of a patient with atopic dermatitis in Case 9 before treatment (a) and after treatment (b)

The patient had been taking various treatments for atopic dermatitis since childhood, but not considerably improved, and thus stopped treatment for a while, but visited the hospital on Aug. 8, 2011. At the visit, he had severe atopic dermatitis all over the body, and particularly, on his back and neck, graded as erythema (3 points), edema (3 points), and excoriation (3 points) by TIS, and lots of pustular papules [refer to FIG. 3(a)].

Two tablets of Lacteol daily were prescribed, but the patient intermittently administered and daily administered two weeks before the visit on October 29. At the second visit, symptoms were milder, and graded as erythema (1 to 2 point), redness (0 to 1 point), and excoriation (2 points) by TIS, and many pustular papules disappeared [refer to FIG. 3(b)].

For a more rapid effect, three tablets of Lacteol were administered daily, and visited the hospital again after 11 days on November 9. He showed improved symptoms graded as erythema (0 to 1 point), edema (0 to 1 point), and excoriation (1 to 2 points) by TIS. There was no side effect regardless of a dose.

Case 10) Cha 00 (f/41)

The patient visited the hospital on Aug. 30, 2011 for lots of erythematous pustular papules (acne) on her face.

Two tablets of Lacteol were administered daily, and at the second visit on October 18, her skin looked clearer and brighter, and lots of lesions disappeared, and there was no side effect.

Case 11) Ok 00 (m/5)

The patient had been suffering from atopic dermatitis for three years, and visited the hospital on Sep. 28, 2011. At the visit, atopic dermatitis was graded as erythema (1 to 2 points), edema (1 point), and excoriation (1 to 2 points) by TIS, and shown on the frontal chest area, and the left side of and behind the neck.

Since his body weight was less than 20 kg, ½ tablet of Lacteol daily was administered. At the second visit on October 22, the symptoms were improved and graded as erythema (0 to 1 point), edema (0 to 1 point), and excoriation (0 to 1 point) by TIS, and there was no discomfort and side effect during administration.

Case 12) Lee 00 (m/3)

The patient had been suffering from atopic dermatitis since an infant, and visited the hospital on Sep. 24, 2011. At the visit, lesions on left and right popliteal fossae were graded as erythema (2 to 3 points), edema (1 to 3 points), and excoriation (2 to 3 points) by TIS.

Since his body weight was less than 20 kg, ½ tablet of Lacteol was administered daily. Since he evacuated the bowels twice or three times a day, he stopped administering Lacteol five days before the visit, and visited the hospital again on November 5. At the second visit, the lesions were considerably improved as erythema (0 to 1 point), edema (0 to 1 point), and excoriation (0 to 1 point) by TIS, but he evacuated the bowels several times and thus stopped administering of Lacteol. After a dosage of Lacteol was reduced to a ¼ tablet daily, there was no side effect any more, and therefore a follow-up is progressing.

Case 13) Kim 00 (m/54)

The patient had been intermittently treated for allergic rhinitis and atopic dermatitis over 20 years, and visited the hospital on Oct. 14, 2011. On the right neck, around the chins, and the left side of the neck, atopic dermatitis was graded as erythema (1 to 2 points), edema (1 to 2 points), and excoriation (1 to 2 points) by TIS, and several papules were shown on both chins. Allergic rhinitis was graded as nasal stuffiness (2 to 3 points), nasal discharge (2 points), nasal itching (2 point)s, sneezing (1 to 2 points), and eye itching (1 to 2 points) by SS.

Two tablets of Lacteol were administered daily, and at the second visit on October 31, the lesions were improved and graded as erythema (0 to 1 point), edema (0 to 1 point), and excoriation (0 to 1 point) by TIS, and almost all of the papules shown on the face disappeared. Each of the SS scores of allergic rhinitis was highly improved by 1 to 2 points, and there was no side effect.

Case 14) Kang 00 (f/51)

The patient had been suffering from atopic dermatitis and cholinergic urticaria over 10 years, and visited the hospital on Sep. 26, 2011. At the visit, lesions were shown on the right face, and the back and neck areas, and showed symptoms graded as erythema (2 to 3 points), edema (1 to 2 points), and excoriation (1 to 2 points) by TIS, and total IgE was increased to 478.4 IU/ml.

Two tablets of Lacteol were administered daily, and at the second visit on November 4, according to the TIS carried out on the lesions, the symptoms were milder and graded as erythema (0 to 1 point), edema (0 to 1 point), and excoriation (0 to 1 point), and total IgE was normal as 7.3 IU/ml.

Case 15) Rho 00 (m/50)

The patient had been applying topical steroids to lesions of severe pruritus triggered by atopic dermatitis over approximately 30 years, and visited the hospital on Oct. 11, 2011. Particularly severe lesions were both shins and chin areas, and showed symptoms graded as erythema (2 to 3 points), edema (2 point), and excoriation (2 to 3 points) by TIS, and there were several papules around both chins. Total IgE was 255.2 IU/ml.

Two tablets of Lacteol daily were prescribed, and at the second visit on November 5, according to TIS carried out on the lesions, the symptoms were considerably milder and graded as erythema (1 to 2 points), edema (1 point), and excoriation (0 to 1 point), and the several papules around the chins were considerably reduced, and scratching on the shin triggered by the severe pruritus was noticeably reduced because of reduction of the pruritus, and thus it was not necessary to use topical steroids any more. Total IgE was reduced to 221.8 IU/ml.

Case 16) Cho 00 (f/33)

The patient had been treated for atopic dermatitis in a dermatology clinic, and visited the hospital on Sep. 26, 2011. At the visit, erythematous patches were shown on both antecubital areas and the neck area, blackheads and small papules were distributed all over both chins and face. According to TIS carried out on the lesions, symptoms were graded as erythema (2 to 3 points), edema (1 to 2 points), and excoriation (1 to 2 points), and total IgE was increased to 211.6 IU/ml.

Two tablets of Lacteol daily were administered, and at the second visit on November 2, according to TIS carried out on the lesions, the symptoms were considerably milder and graded as erythema (0 to 1 point), edema (0 to 1 point), and excoriation (0 point), and the heads and papules on the face were considerably reduced. Total IgE was reduced to 184 IU/ml, and there was no side effect during administration.

Case 17) Cho 00 (f/25)

The patient had been suffering from mild pruritus and erythematous patch on her face and chins over two years, and visited the hospital on Sep. 15, 2011. At the visit, according to TIS carried out on the lesions on the forehead, both sides of the face, and around the chins, symptoms were graded as erythema (1 to 2 points), edema (1 to 2 points), and excoriation (0 to 1 point), and many small papules were observed all over the face and forehead.

Two tablets of Lacteol were administered daily, and at the second visit on October 29, according to the TIS carried out on the lesions, the symptoms were milder and graded as erythema (0 to 1 point), edema (0 to 1 point), and excoriation (0 point), lots of the small papules distributed on the face and forehead disappeared, and the face became brighter overall.

Case 18) Kim 00 (m/10)

Figure 4:
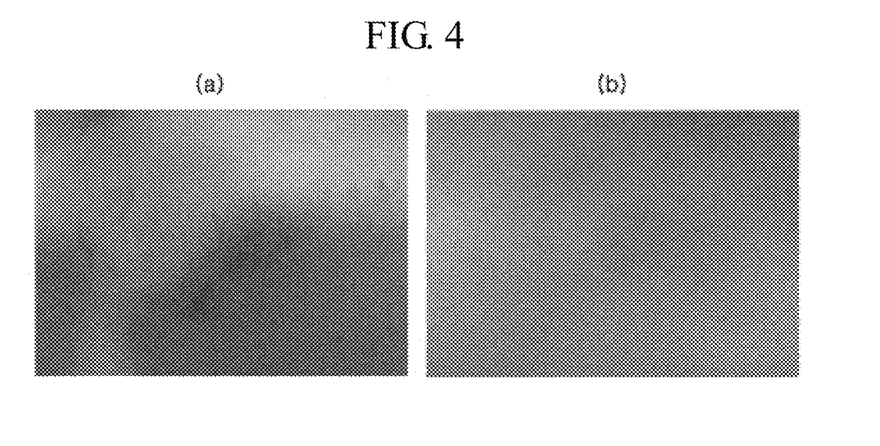
FIG. 4 shows images of the back area of a patient with atopic dermatitis in Case 18 before treatment (a) and after treatment (b)

The patient had been treated for atopic dermatitis for a long time, and visited the hospital on Oct. 22, 2011. Overall, he had severe lesions on the arms, the legs, the neck, the face, and particularly sever lesions on an upper part of the back [refer to FIG. 4(a)]. According to TIS carried out on the lesions, symptoms were graded as erythema (2 to 3 points), edema (2 to 3 points) and excoriation (2 to 3 points) (particularly, crust and oozing triggered by severe scratching were shown on the upper part of the back).

Since his body weight was over 50 kg, two tablets of Lacteol daily were prescribed. At the second visit on November 11, after approximately 20 days of the first visit, according to TIS carried out on the lesions, symptoms were noticeably improved and graded as erythema (0 to 1 point), edema (1 point), and excoriation (0 to 1 point) [particularly, the lesion on the upper part of the back was almost all disappeared, (refer to FIG. 4(b)] within a short period, and there was no side effect.

Case 19) Han 00 (f/22)

The patient had been suffering from allergic rhinitis for a long time since a child, and visited the hospital on Sep. 26, 2011. According to SS, allergic rhinitis was graded as nasal stuffiness (3 points), nasal discharge (2 point), nasal itching (2 points), and sneezing (3 points), atopic dermatitis was shown on the face and the back side of the ears and graded as erythema (2 to 3 points), edema (1 to 2 points), and excoriation (1 point) by TIS, and there were many papules and pustular papules on the forehead.

Two tablets of Lacteol daily were prescribed, and at the second visit on November 4, according to SS, allergic rhinitis was improved and graded as nasal stuffiness (1 point), nasal discharge (1 point), nasal itching (1 point), and sneezing (1 point), the atopic lesions were improved and graded as erythema (0 to 1 point), edema (0 to 1 point), and excoriation (0 point) by TIS, and lots of the papules and pustular papules on the forehead and chins seemed disappeared.

Case 20) Bang 00 (m/25)

The patient had been treated for psoriasis since a child, had been suffering from allergic rhinitis symptoms (nasal stuffiness, nasal discharge, and conjunctival itching sense) for 2 to 3 years, and visited the hospital on Aug. 11, 2011. At the visit, according to SS, allergic rhinitis was graded as nasal stuffiness (2 to 3 points), nasal discharge (1 to 2 points), nasal itching (2 points), sneezing (2 points), eye itching (2 points), and eye redness (1 point), and total IgE was measured at 213.7 IU/ml. Psoriasis did not have apparent improvement compared to the past, and intermittent treatment was in progress.

Two tablets of Lacteol daily were prescribed, and at the second visit on September 28, according to SS, allergic rhinitis was graded as nasal stuffiness (1 point), nasal discharge (0 to 1 point), nasal itching (1 point), sneezing (1 point), eye itching (1 point), and eye redness (0 to 1 point), total IgE was considerably reduced to 94.7 IU/ml, and there was no side effect caused by the administration of Lacteol.

Case 21) Yang 00 (f/39)

The patient had intermittently taken antihistamines for allergic rhinitis and allergic conjunctivitis under a doctor's opinion for 3 to 4 years, and visited the hospital on Aug. 23, 2011. At the visit, according to SS, allergic rhinitis was graded as nasal stuffiness (2 to 3 points), nasal discharge (2 points), nasal itching (2 points), sneezing (2 points), eye itching (2 points), eye redness (1 point), and eye tearing (1 point), and total IgE was 360.6 IU/ml.

Two tablets of Lacteol daily were prescribed, and at the second visit on September 26, according to SS, allergic rhinitis was graded as nasal stuffiness (1 point), nasal discharge (1 point), nasal itching (1 point), sneezing (1 point), eye itching (0 to 1 point), eye redness (0 point), and eye tearing (0 point), and total IgE was considerably reduced to 247.9 IU/ml. During administration of Lacteol, constipation that had been previously suffered was a little deteriorated, but not so much severe as to stop administering of Lacteol. During a 2-month follow-up in an outpatient unit, there was no discontinuation of the drug administration due to side effects.

Case 22) Kim 00 (m/39)

The patient had intermittently taken antihistamines to reduce symptoms of allergic rhinitis and allergic conjunctivitis under a doctor's opinion, and visited the hospital on Aug. 23, 2011. According to SS, allergic rhinitis was graded as nasal stuffiness (2 points), nasal discharge (2 points), nasal itching (3 points), sneezing (2 points), eye itching (3 points), eye redness (1 to 2 points), eye tearing (2 points), and ears itching (2 points), and total IgE was 182.1 IU/ml.

Two tablets of Lacteol daily were prescribed, and at the second visit on September 29, according to SS, allergic rhinitis was graded as nasal stuffiness (1 point), nasal discharge (1 point), nasal itching (1 to 2 points), sneezing (1 point), eye itching (1 point), eye redness (0 to 1 point), eye tearing (0 to 1 point), and ears itching (0 to 1 point), and total IgE was reduced to 150.2 IU/ml. Compared to other patients, a relatively smaller decrease in total IgE was considered to be correlated with the administration of the antihistamines before the visit.

Case 23) Son 00 (m/38)

The patient had been suffering from allergic rhinitis for 8 to 9 years, and visited the hospital on August 19. At the visit, according to SS, allergic rhinitis was graded as nasal stuffiness (2 to 3 points), nasal discharge (2 points), nasal itching (2 points), and sneezing (2 points), atopic dermatitis on the face and the ear lobes was graded as erythema (2 to 3 points), edema (1 to 2 points) and excoriation (0 to 1 point) by TIS, and total IgE was measured at 301.8 IU/ml.

Two tablets of Lacteol daily were prescribed, and at the second visit on September 28, according to SS, allergic rhinitis was graded as nasal stuffiness (1 to 2 points), nasal discharge (1 point), nasal itching (1 point), and sneezing (1 point), atopic dermatitis was improved and graded as erythema (0 to 1 point), edema (1 point), excoriation (0 point) by TIS, total IgE was reduced to 249.8 IU/ml, and there was no side effect.

Case 24) Go 00 (f/35)

The patient had been suffering from atopic dermatitis over 20 years, accompanied with allergic rhinitis for 9 years, and visited the hospital on Sep. 6, 2011. At the visit, atopic dermatitis was graded as erythema (2 to 3 points), edema (1 to 2 points), and excoriation (2 point) by TIS, accompanied with blackheads and many papules on her face, and main lesions of atopic dermatitis were distributed around the neck and the antecubital fossa. Allergic rhinitis was graded as nasal stuffiness (2 points), nasal discharge (1 to 2 points), nasal itching (2 points), and sneezing (2 points) by SS, and total IgE was increased to 568.5 IU/ml.

Two tablets of Lacteol daily was prescribed, and at the second visit on October 10, atopic dermatitis was graded as erythema (0 to 1 point), edema (1 point), and excoriation (0 to 1 point) by TIS, and lots of blackheads and papules were decreased. Allergic rhinitis was graded as nasal stuffiness (0 to 1 point), nasal discharge (0 to 1 point), nasal itching (1 point), and sneezing (1 point) by SS, which indicated that the symptoms became milder, and total IgE was reduced to 469.1 IU/ml.

Case 25) Kim 00 (f/22)

Figure 5:
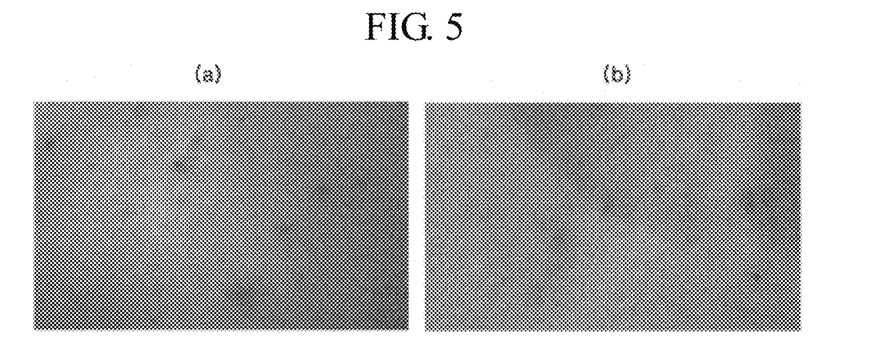
FIG. 5 shows images of antecubital fossa of a patient with atopic dermatitis in Case 25 before treatment (a) and after treatment (b)
Figure 6:
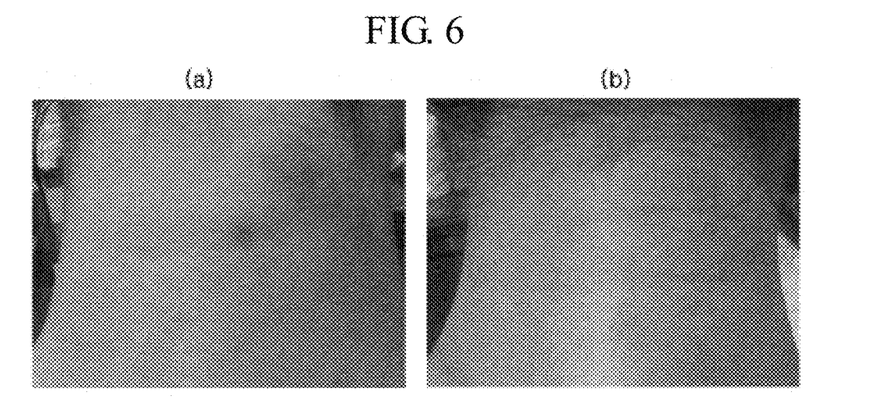
FIG. 6 shows images of the back side of the neck of a patient with atopic dermatitis in Case 25 before treatment (a) and after treatment (b)

The patient had been suffering from atopic dermatitis for 20 years, had been treated for allergic rhinitis symptoms for 10 years, but had no improvement, and thus visited the hospital on Sep. 23, 2011. Atopic dermatitis on the lesions on the neck, forehead, face, lip, both antecubital fossae, etc. [refer to FIGS. 5(a) and 6(a)] was graded as erythema (3 points), edema (3 points), and excoriation (3 points—accompanied with crust and oozing provoked by severe scratching) by TIS, allergic rhinitis was graded as nasal stuffiness (2 to 3 points), nasal discharge (3 points), nasal itching (3 points), sneezing (2 points), eye itching (2 points), and eye tearing (2 point) by SS, and total IgE was high as 2434.8 IU/ml.

Two tablets of Lacteol daily were prescribed, at the second visit on October 20, the lesions were improved, and total IgE was considerably reduced to 2087.8 IU/ml.

To increase a therapeutic effect, three tablets of Lacteol daily were prescribed, and the patient visited thirdly the hospital on November 11. At the third visit, atopic dermatitis was graded as erythema (1 point), edema (1 point), and excoriation (1 point) by TIS, many papules distributed on the forehead, crusts on the lip, and scales distributed all over the face were considerably decreased [refer to FIG. 5(b) and FIG. 6(b)]. Allergic rhinitis was graded as nasal stuffiness (1 point), nasal discharge (1 point), nasal itching (1 point), sneezing (1 point), eye itching (1 point), and eye tearing (1 point) by SS, which indicated that allergic rhinitis was considerably improved, and as a dosage increased, the lesions seemed to be more rapidly improved. There was no side effect due to the change in dosage during the administration of Lacteol.

Case 26) Kim 00 (f/30)

The patient had been treated for atopic dermatitis for a long time, but not improved. Recently, as lesions on fingers became worse, she was difficult to do kitchen works, and thus visited the hospital on Sep. 24, 2011. Main lesions of atopic dermatitis were both fingers, neck area, lip-fringe, and both antecubital fossae, and atopic dermatitis was graded as erythema (2 to 3 points), edema (1 to 2 points), and excoriation (2 to 3 points) by TIS.

Two tablets of Lacteol daily were prescribed, at the second visit on November 5, the lesions were considerably improved and graded as erythema (0 to 1 point), edema (0 to 1 point) and excoriation (0 to 1 point) by TIS. Because of the improvement of the lesions, she could do kitchen works.

Case 27) Kim 00 (f/68)

The patient had been treated for diabetes and high blood pressure in an outpatient unit, also treated for allergic rhinitis, allergic conjunctivitis, and skin pruritus in the departments of dermatology and ophthalmology for 4 to 5 years, and visited the hospital on Aug. 25, 2011. Allergic rhinitis was graded as nasal stuffiness (2 points), nasal discharge (1 to 2 points), nasal itching (3 points), sneezing (2 points), eye itching (2 points), eye tearing (2 points), and eye redness (1 to 2 points) by SS, and erythema was shown on the face and ear areas. Total IgE was increased to 536 IU/ml.

Two tablets of Lacteol daily were prescribed, and at the second visit on September 29, the total IgE was reduced to 317.6 IU/ml, and at the third visit on October 31, the total IgE was reduced again to 287.4 IU/ml, allergic rhinitis was graded as nasal stuffiness (0 to 1 point), nasal discharge (0 to 1 point), nasal itching (1 point), sneezing (1 point), eye itching (0 to 1 point), eye tearing (0 to 1 point), and eye redness (0 to 1 point) by SS, which indicated that allergic rhinitis was improved, almost all of the erythema shown on her face and ear areas disappeared, and thus a color of the areas became brighter. There was no specific side effect.

Case 28) Kim 00 (m/32)

The patient had been treated for allergic rhinitis for 3 to 4 years, but had not improved, and thus visited the hospital on Sep. 21, 2011. Allergic rhinitis was graded as nasal stuffiness (2 points), nasal discharge (2 points), nasal itching (2 points), sneezing (2 points), eye itching (2 points), and eye redness (2 points) by SS, total IgE was increased to 476.6 IU/ml, erythema was shown on his face and forehead, and many papules and blackheads were shown overall.

Two tablets of Lacteol daily were prescribed, and at the second visit on October 19, allergic rhinitis was graded as nasal stuffiness (1 point), nasal discharge (1 point), nasal itching (1 point), sneezing (1 point), eye itching (1 point), and eye redness (1 point) by SS, which indicated that allergic rhinitis was improved, the erythema shown on his face and forehead, the papules, and the blackheads were decreased, and total IgE was reduced to 408.6 IU/ml.

Case 29) Kim 00 (m/29)

The patient had been treated for psoriasis for a long time, but stopped treatment because of no improvement. However, since pruritus generated 2 to 3 years ago became worse, he visited the hospital on Oct. 21, 2011. Main lesions of atopic dermatitis were the neck, the face, and the back of ears, and atopic dermatitis was graded as erythema (2 to 3 points), edema (1 to 2 points), and excoriation (1 to 2 points) by TIS. The psoriasis was accompanied with atomic dermatitis behind the right ear, and erythema, pustular papule, and erythematous papule were distributed on the chin area.

Two tablets of Lacteol daily were prescribed, and at the second visit on November 10, the lesions seemed improved. Since total IgE carried out at the visit was checked in a high level of 1978.4 IU/ml, a dosage of Lacteol was increased to three tablets daily to improve a therapeutic effect.

At the third visit on November 15, atopic dermatitis was graded as erythema (0 to 1 point), edema (0 to 1 point), excoriation (0 to 1 point) by TIS, which indicated that atopic dermatitis was improved, erythema, pustular papule, and erythematous papule shown around the chins were decreased a lot, total IgE carried out again was reduced to 1735.6 IU/ml, and the pruritus appealed at the first visit was much milder.

Case 30) Woo 00 (m/30)

The patient had intermittently administered antihistamines for pruritus generated 4 to 5 years ago, and visited the hospital on Sep. 26, 2011 due to the worsening of pruritus. Main lesions of atopic dermatitis were the face and the back of the ears, atopic dermatitis was graded as erythema (2 to 3 points), edema (1 to 2 points), and excoriation (1 to 2 points) by TIS, and total IgE was measured in the high level of 202 IU/ml.

Two tablets of Lacteol daily were prescribed, and at the second visit on October 28, atopic dermatitis was graded as erythema (0 to 1 point), edema (0 to 1 point), and excoriation (0 to 1 point) by TIS, lots of the erythema behind his ears and the small papules on his face were reduced, and the total IgE carried out again was reduced to 155.7 IU/ml.

Case 31) Song 00 (f/60)

The patient had been intermittently treated for allergic rhinitis since moving to an old apartment 10 years ago, and visited the hospital on Sep. 29, 2011. Allergic rhinitis was graded as nasal stuffiness (2 points), nasal discharge (1 to 2 points), nasal itching (2 points), sneezing (2 points), and eye itching (2 points) by SS, and total IgE was increased to 393.6 IU/ml.

Two tablets of Lacteol daily were prescribed, and at the second visit on October 31, allergic rhinitis was improved and graded as nasal stuffiness (1 point), nasal discharge (0 to 1 point), nasal itching (1 point), sneezing (1 point), and eye itching (1 point) by SS, and the total IgE carried out again was reduced to 272.4 IU/ml.

Case 32) Kim 00 (m/56)

The patient had been treated for abnormal blood pressure and diabetes in the hospital, had intermittently administered antihistamines for allergic rhinitis and pruritus for two years, and visited the hospital on Oct. 13, 2011 due to the worsening of allergic rhinitis and pruritus. Allergic rhinitis was graded as nasal stuffiness (2 to 3 points), nasal discharge (2 points), nasal itching (2 points), sneezing (3 points), eye itching (2 points), eye redness (1 to 2 points), and eye tearing (2 points) by SS, and erythema and mild edema on both antecubital fossae, and erythema and many erythematous papules distributed around the chins were shown.

Two tablets of Lacteol daily were prescribed, and at the second visit on November 15, allergic rhinitis was improved and graded as nasal stuffiness (1 point), nasal discharge (1 point), nasal itching (1 point), sneezing (1 point), eye itching (1 point), eye redness (0 to 1 point), and eye tearing (1 point) by SS, and the erythema and mild edema on both antecubital fossae, and the erythema and papules around the chins considerably disappeared.

Case 33) Baek 00 (m/10)

The patient had been suffering from allergic rhinitis and pruritus since childhood, and visited the hospital on Oct. 11, 2011. Allergic rhinitis was graded as nasal stuffiness (2 points), nasal discharge (2 to 3 points), nasal itching (2 points), and sneezing (2 points) by SS, the main lesions of atopic dermatitis were his face and forehead, and atopic dermatitis was graded as erythema (1 to 2 points), edema (1 point), and excoriation (1 point) by TIS. Dryness, some scales, and many papules were distributed on his face and forehead areas.

Since his body weight was 25 kg, which was less than 40 kg, one tablet of Lacteol daily was prescribed, at the second visit on November 10, allergic rhinitis was improved and graded as nasal stuffiness (1 point), nasal discharge (1 point), nasal itching (1 point), and sneezing (1 point) by SS, atopic dermatitis on the lesions was improved and graded as erythema (0 to 1 point), edema (0 point), and excoriation (0 point), and the dryness, some scales, and many papules shown on the lesions disappeared, and there was no specific side effect.

Case 34) Kim 00 (m/61)

The patient had been treated for diabetes and high blood pressure, had continuously administered antihistamines due to pruritus started from approximately 2 years ago, and visited the hospital on Aug. 4, 2011 due to the worsening of symptoms. The main lesions of atopic dermatitis were the face area and both antecubital fossae, and TIS scores of atopic dermatitis were graded as erythema (2 to 3 points), edema (1 to 2 points), and excoriation (1 to 2 points).

Two tablets of Lacteol daily were prescribed, and at the second visit on November 5, atopic dermatitis on the main lesions were improved and graded as erythema (0 to 1 point), edema (0 to 1 point), and excoriation (0 to 1 point) by TIS, and the frequently-administered antihistamines were barely used, and during treatment, antihypertensive agents, antihyperlipidemic agents, and antidiabetic agents were also used, and there were no specific side effects caused by drug interactions.

Results of Clinical Trials

1) Considerable Decrease in Total IgE

Total IgE before and after treatment was measured in 22 adult patients consenting to blood gathering among 34 patients with severe atopic dermatitis or allergic rhinitis to demonstrate therapeutic effects.

Among the 22 patients, in the patients in Cases 4 and 8 that had the total IgE value was 91 IU/ml or less, which was the same as the value of a normal adult, the measurement of total IgE was not applied thereto, and changes in total IgE were examined in the rest of the patients except the patients in Cases 7, 15, 16, and 22 to which antihistamines, steroid ointments, etc. were used to improve allergic diseases before treatment.

Figure 7:
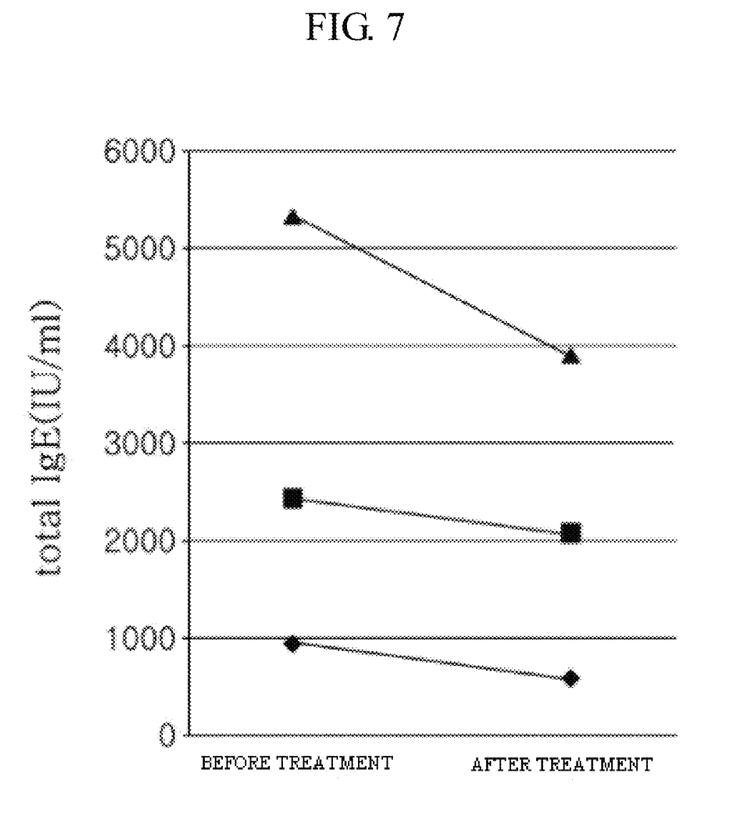
FIG. 7 is a graph showing a change in total IgE before and after treatment of a patient with a severe allergic disease, in which a value of the total IgE before treatment is 900 IU/ml or more.
Figure 8:
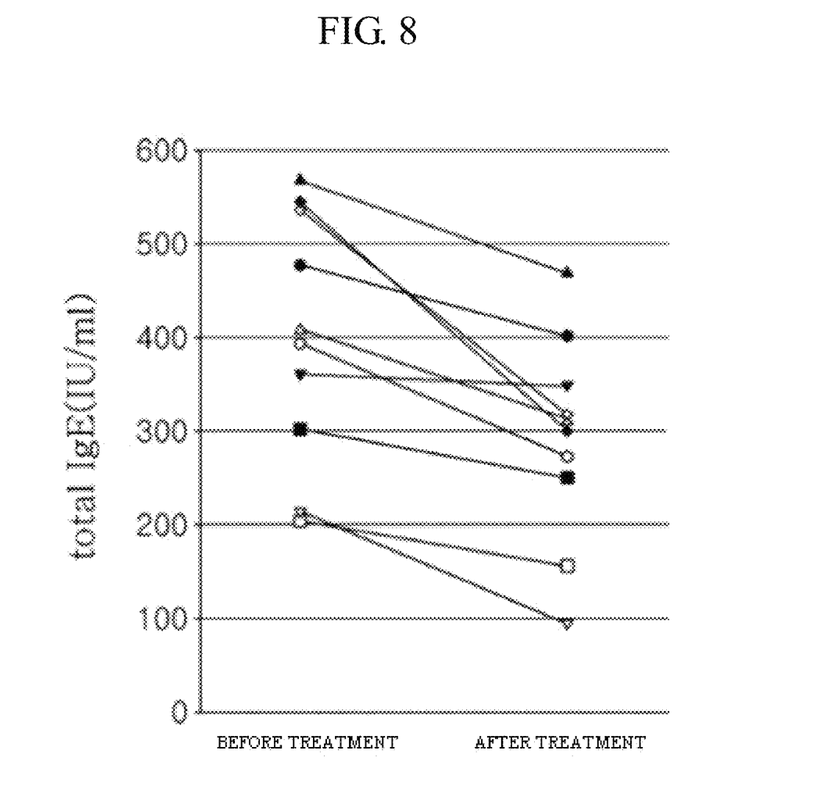
FIG. 8 is a graph showing a change in total IgE before and after treatment of a patient with an allergic disease, in which a value of the total IgE before treatment is 100 to 900 IU/ml.

First, FIG. 7 shows the change in total IgE before and after treatment in the patient with a very severe allergic disease having a value of total IgE before treatment of 900 IU/ml or more, and FIG. 8 shows changes in total IgE before and after treatment in other patients. In all of the patients in FIGS. 7 and 8, total IgE values were considerably decreased after treatment, and thus it was confirmed that Lacteol was effective in treating an IgE-mediated allergic disease.

2) Decrease in TIS Scales of Patients with Atopic Dermatitis

Among the 34 patients, the number of patients with atopic dermatitis was 23, and values of the TIS scale before and after treatment were compared. The results are listed in Table 1.

TABLE 1

| Case No. | Before treatment | After treatment |
|---|---|---|
| 1 | 9 | 4.5 |
| 2 | 6.5 | 1.5 |
| 6 | 5.5 | 1.5 |
| 7 | 4 | 0.5 |
| 8 | 7.5 | 0.5 |
| 9 | 9 | 4 |
| 11 | 4 | 1.5 |
| 12 | 7 | 1.5 |
| 13 | 4.5 | 1.5 |
| 14 | 5.5 | 1.5 |
| 15 | 7 | 3 |
| 16 | 5.5 | 1 |
| 17 | 4 | 1 |
| 18 | 7.5 | 2 |
| 19 | 5 | 1 |
| 23 | 4.5 | 1.5 |
| 24 | 6 | 2 |
| 25 | 9 | 3 |
| 26 | 7.5 | 1.5 |

TABLE 1-continued

| Case No. | Before treatment | After treatment |
|---|---|---|
| 29 | 5.5 | 1.5 |
| 30 | 5.5 | 1.5 |
| 33 | 4.5 | 0.5 |
| 34 | 5.5 | 1.5 |

It was confirmed that, in the patients with severe atopic dermatitis of a mean severity of 6.1 before treatment, after 1 to 2-month treatment, atopic dermatitis was considerably improved to a mild form having a severity of 1.7.

3) Decrease in SS Scales of Patients with Allergic Rhinitis

Among the 34 patients, the number of patients with allergic rhinitis was 16, and values of the SS scale before and after treatment were compared. The results are listed in Table 2.

TABLE 2

| Case No. | Before treatment | After treatment |
|---|---|---|
| 2 | 7 | 0 |
| 3 | 10 | 4 |
| 5 | 15.5 | 5.5 |
| 13 | 9.5 | 3.5 |
| 19 | 10 | 4 |
| 20 | 11 | 5 |
| 21 | 12.5 | 4.5 |
| 22 | 17.5 | 7.5 |
| 23 | 8.5 | 4.5 |
| 24 | 7.5 | 3 |
| 25 | 14.5 | 6 |
| 27 | 13 | 4.5 |
| 28 | 12 | 6 |
| 31 | 9.5 | 4.5 |
| 32 | 15 | 6.5 |
| 33 | 8.5 | 4 |

It was confirmed that severities of the patients with allergic rhinitis were considerably improved to 4.6 after treatment from averagely 11.3 before treatment.

4) Other Improved Effects

In addition to the atopic dermatitis and allergic rhinitis, in the patients of Cases 4 and 14, urticaria was improved, in the patients of Cases 5, 21, 22, and 27, improvement in allergic conjunctivitis was confirmed, and in the patients of Cases 10, 16, 24, and 28, improvement in acne was confirmed.

5) Side Effects

There was no case reporting noticeable side effects such as constipation and abdominal distention during the treatment of the 34 patients. However, in the three-year-old infant of Case 12, when ½ tablet of Lacteol was administered daily, loose stool was shown, and thus a dosage was reduced to a ¼ tablet.

6) Conclusion

While living cells of Lactobacilli such as *Lactobacillus acidophilus* L-92, *Lactobacillus rhamnosus* GG, *Lactobacillus reuteri*, *Lactobacillus fermentum*, *Lactobacillus acidophilus* DDS-1, *Lactobacillus acidophilus* NCFM, etc. are known to be effective in allergic diseases (atopic dermatitis, allergic rhinitis, urticaria, etc), acne, or skin improvement, satisfactory noticeable therapeutic effects thereof were not reported in clinical trials with respect to humans.

Lacteol is dead cells, not living cells, of *Lactobacillus acidophilus* LB strain, and known to be effective only in acute diarrhea and diarrhea caused by a functional bowel disorder, but according to the trial results, it showed very excellent efficacy in allergic diseases including IgE-mediated and non-IgE-mediated atopic dermatitis, allergic rhinitis, urticaria, and allergic conjunctivitis, and acne.

The pharmaceutical composition of the present invention includes dead cells of *Lactobacillus acidophilus* LB strain as an active ingredient, and thus reduces total IgE contents in the blood without a side effect. Therefore, it can be used to treat and prevent IgE-mediated allergic diseases and non-IgE-mediated allergic diseases, for example, atopic dermatitis, allergic rhinitis, allergic conjunctivitis, urticaria, or pollinosis.

While the invention has been shown and described with reference to certain exemplary embodiments thereof, it will be understood by those skilled in the art that various modifications in form and details may be made therein without departing from the spirit and scope of the invention as defined by the appended claims.

What is claimed is:

1. A method of treating or inhibiting an allergic disease, said method comprising:
   providing a pharmaceutical composition comprising a therapeutically effective amount of dead cells of *Lactobacillus acidophilus* LB strain as an active ingredient; and
   administering the pharmaceutical composition to a human subject to reduce total IgE contents in the blood, wherein the allergic disease is treated or inhibited,
   wherein the therapeutically effective amount of the composition is orally administered to the human subject on a single day for more than 2 weeks,
   wherein the dead cells are prepared in the form of a culture solution containing tyndallized dead cells of *Lactobacillus acidophilus* LB strain.

2. The method according to claim 1, wherein the dead cells are prepared in the form of a freeze-dried product of the culture solution containing tyndallized dead cells of *Lactobacillus acidophilus* LB strain.

3. The method according to claim 1, wherein the allergic disease is atopic dermatitis, allergic rhinitis, allergic conjunctivitis, urticaria, pollinosis, or asthma.

4. The method according to claim 1, wherein the dead cells are made in the form of a tablet, a capsule, a granule, a powder, or a liquid.

5. The method according to claim 1, wherein a three item severity (TIS) scale is reduced after the administering step.

6. The method according to claim 1, wherein the composition is orally administered in an amount of 1 to 10 billion cells.

* * * * *